US 7,447,566 B2

(12) United States Patent
Knauper et al.

(10) Patent No.: US 7,447,566 B2
(45) Date of Patent: Nov. 4, 2008

(54) OCCLUSION SYSTEM AND METHOD FOR A FLOW CONTROL APPARATUS

(75) Inventors: Christopher A. Knauper, O'Fallon, MO (US); Joseph A. Hudson, O'Fallon, MO (US)

(73) Assignee: Covidien AG (CH)

( * ) Notice: Subject to any disclaimer, the term of this patent is extended or adjusted under 35 U.S.C. 154(b) by 167 days.

(21) Appl. No.: 11/464,429

(22) Filed: Aug. 14, 2006

(65) Prior Publication Data

US 2007/0083292 A1     Apr. 12, 2007

Related U.S. Application Data

(63) Continuation-in-part of application No. 10/853,926, filed on May 25, 2004, now Pat. No. 7,092,797.

(51) Int. Cl.
*G05D 7/00*     (2006.01)
*A61M 31/00*    (2006.01)

(52) U.S. Cl. .............................. 700/282; 128/DIG. 13; 604/67

(58) Field of Classification Search ................ 700/282; 604/65, 67, 153; 128/DIG. 13
See application file for complete search history.

(56) References Cited

U.S. PATENT DOCUMENTS

| | | | |
|---|---|---|---|
| 4,504,263 A | 3/1985 | Steuer et al. | |
| 4,583,975 A | 4/1986 | Pekkarinen et al. | |
| 4,672,997 A * | 6/1987 | Landis et al. | 137/554 |
| 4,820,281 A | 4/1989 | Lawler, Jr. | |
| 4,845,487 A | 7/1989 | Frantz et al. | |
| 4,869,722 A | 9/1989 | Heyman | |
| 4,919,596 A * | 4/1990 | Slate et al. | 417/18 |
| 4,959,050 A | 9/1990 | Bobo, Jr. | |
| 5,039,279 A | 8/1991 | Natwick et al. | |
| 5,049,047 A | 9/1991 | Polaschegg et al. | |
| 5,135,485 A | 8/1992 | Cohen et al. | |
| 5,213,573 A | 5/1993 | Sorich et al. | |
| 5,292,306 A | 3/1994 | Wynkoop et al. | |
| 5,423,746 A | 6/1995 | Burkett et al. | |
| 5,438,510 A | 8/1995 | Bryant et al. | |
| 5,464,392 A | 11/1995 | Epstein et al. | |
| 5,551,850 A | 9/1996 | Williamson et al. | |
| 5,562,615 A | 10/1996 | Nassif | |
| 5,563,584 A | 10/1996 | Rader et al. | |
| 5,584,811 A | 12/1996 | Ross et al. | |
| 5,695,473 A | 12/1997 | Olsen | |
| 5,720,721 A | 2/1998 | Dumas et al. | |
| 5,807,322 A * | 9/1998 | Lindsey et al. | 604/65 |

(Continued)

FOREIGN PATENT DOCUMENTS

EP     1 466 637 A2     10/2004

(Continued)

*Primary Examiner*—Albert DeCady
*Assistant Examiner*—Steven R Garland
(74) *Attorney, Agent, or Firm*—Edward S. Jarmolowicz, Esq.

(57) ABSTRACT

A flow control apparatus having a flow monitoring system capable of detecting and identifying a downstream occlusion present within an administration feeding set loaded to the flow control apparatus is disclosed. A software subsystem is associated with the flow control apparatus and administration feeding set, the software system plots at least one discrete date point against a standard occlusion profile to detect if a downstream occlusion present within the administration feeding set.

5 Claims, 15 Drawing Sheets

U.S. PATENT DOCUMENTS

| | | |
|---|---|---|
| 5,843,035 A | 12/1998 | Bowman et al. |
| 5,853,386 A | 12/1998 | Davis et al. |
| 5,943,633 A | 8/1999 | Wilson et al. |
| 5,951,510 A | 9/1999 | Barak |
| 6,068,612 A | 5/2000 | Bowman et al. |
| RE36,871 E | 9/2000 | Epstein et al. |
| 6,203,528 B1 * | 3/2001 | Deckert et al. .............. 604/131 |
| 6,280,408 B1 | 8/2001 | Sipin |
| 6,491,661 B1 | 12/2002 | Boukhny et al. |
| 6,523,414 B1 | 2/2003 | Malmstrom et al. |
| 6,622,542 B2 | 9/2003 | Derek et al. |
| 6,890,291 B2 | 5/2005 | Robinson et al. |
| 6,942,637 B2 | 9/2005 | Cartledge et al. |
| 2002/0151838 A1 | 10/2002 | Beck et al. |
| 2004/0133166 A1 * | 7/2004 | Moberg et al. .............. 604/151 |

FOREIGN PATENT DOCUMENTS

| | | |
|---|---|---|
| WO | 96/03168 A1 | 2/1996 |
| WO | 01/72357 A2 | 10/2001 |
| WO | 02/38204 A2 | 5/2002 |

* cited by examiner

* - discrete data point

OCCLUSION SYSTEM AND METHOD FOR A FLOW CONTROL APPARATUS

FIELD OF THE INVENTION

The present invention relates to a flow control apparatus capable of identifying a downstream occlusion condition within an administration feeding set.

BACKGROUND OF THE INVENTION

Administering fluids containing medicine or nutrition to a patient is generally well known in the art. Typically, fluid is delivered to the patient by an administration feeding set loaded to a flow control apparatus, such as a pump, connected to a source of fluid which delivers fluid to a patient.

A flow control apparatus of the prior art may also be capable of monitoring and detecting fluid flow conditions that can occur within the loaded administration feeding set during operation of the flow control apparatus. Generally, prior art flow monitoring systems that are capable of monitoring and detecting flow conditions may rely on separate sensors being placed at the upstream and downstream sides of the administration feeding set in order to distinguish between an upstream or a downstream flow condition.

Therefore, there is a need in the art for an improved flow control apparatus having a flow monitoring system capable of identifying between an upstream flow condition and a downstream flow condition using a single sensor, thereby making it possible to monitor the flow of the fluid and recognize any problem that has occurred in the delivery of the fluid.

SUMMARY OF THE INVENTION

The present invention relates to a flow control apparatus comprising a flow control apparatus adapted to be loaded with an administration feeding set having an upstream side and a downstream side, a single sensor for detecting the presence or absence of fluid in the upstream side of the administration feeding set, and a software subsystem in operative association with the single sensor, wherein the software subsystem is capable of identifying between an upstream flow condition and a downstream flow condition present within the administration feeding set.

The present invention also relates to a flow control apparatus comprising a flow control apparatus adapted to be loaded with an administration feeding set, an administration feeding set having an upstream side and a downstream side with the administration feeding set loaded to the flow control apparatus, a single sensor for detecting the presence or absence of fluid in the upstream side of the administration feeding set, and a software subsystem in operative association with the single sensor, wherein the software subsystem is capable of identifying between an upstream flow condition and downstream flow condition present within the administration feeding set loaded to the flow control apparatus.

The present invention further relates to a method for monitoring fluid flow comprising engaging one end of an administration feeding set to at least one fluid source, loading the administration feeding set to a flow control apparatus, engaging another end of the administration feeding set, and identifying between an upstream flow condition and a downstream flow condition present within the administration feeding set loaded to the flow control apparatus.

The system and method is a downstream occlusion (DSO) triggering test that incorporates a standard occlusion profile to determine an occluded feeding tube. The DSO triggering test is invoked through software or user initiated. The DSO triggering test is based on relative rotor turn durations, in milli-seconds (ms), and consecutive rotor turns, measured in turns, as compared against a standard profile for the flow control apparatus.

As the flow control apparatus is running, the system is determining the time of a rotor revolution until the microprocessor receives the required number of encoder signals, which is representative of one complete rotor turn. The system tracks a number of relative revolution durations over apparatus' period of operation, as discrete data points and each data point is compared against the standard occlusion profile, as shown in FIG. 6B or FIG. 6C. The system can set an alarm based on an occlusion detected condition, or control will pass to step 289 in FIG. 4 to determine an occlusion, when the system determines an increase in the relative rotor revolution duration time over one or more rotor turns, or if the duration time matches a standard occlusion profile.

In the first embodiment, a number of revolution times are stored in a revolution history buffer. The buffer, when filled, is averaged and compared against the next NewTime to determine an actual relative rotor duration time difference. This time difference or discrete data point is compared against the standard profile over one or more rotor turns. If compared over a number of rotor turns, and the system is trending higher, the occlusion detected sets the occlusion alarm, or the main control loop exits to step 289 in FIG. 4, to determine the occlusion. If the duration time selected to be a single discrete data point and it meets the standard profile at a single rotor turn, the occlusion detected condition sets the alarm on, to sound.

The next NewTime or rotor revolution time can be filtered (as described in the detailed specification). The DSO Triggering test is used to identify an occlusion state or condition sooner than the procedure, described in FIG. 4, and DOS Triggering operates as a stand alone occlusion detection (as shown in FIG. 10), or the main control loop can exit to step 289 at FIG. 4, as described in an alternative embodiment below in FIG. 11.

The standard profile is stored as computer instructions. The instructions can be a quadratic equation or a data table of points. The profile is loaded into flash memory at the start of the pump. Alternatively the standard profile may be constructed during a pumping operation, such as flushing, by tallying a series of relative rotor durations by consecutive rotor turns and storing them in an array or buffer location. The program may also save this alternative standard profile to an EEPROM for later use.

DETAILED DESCRIPTION OF THE INVENTION

Figure 1:
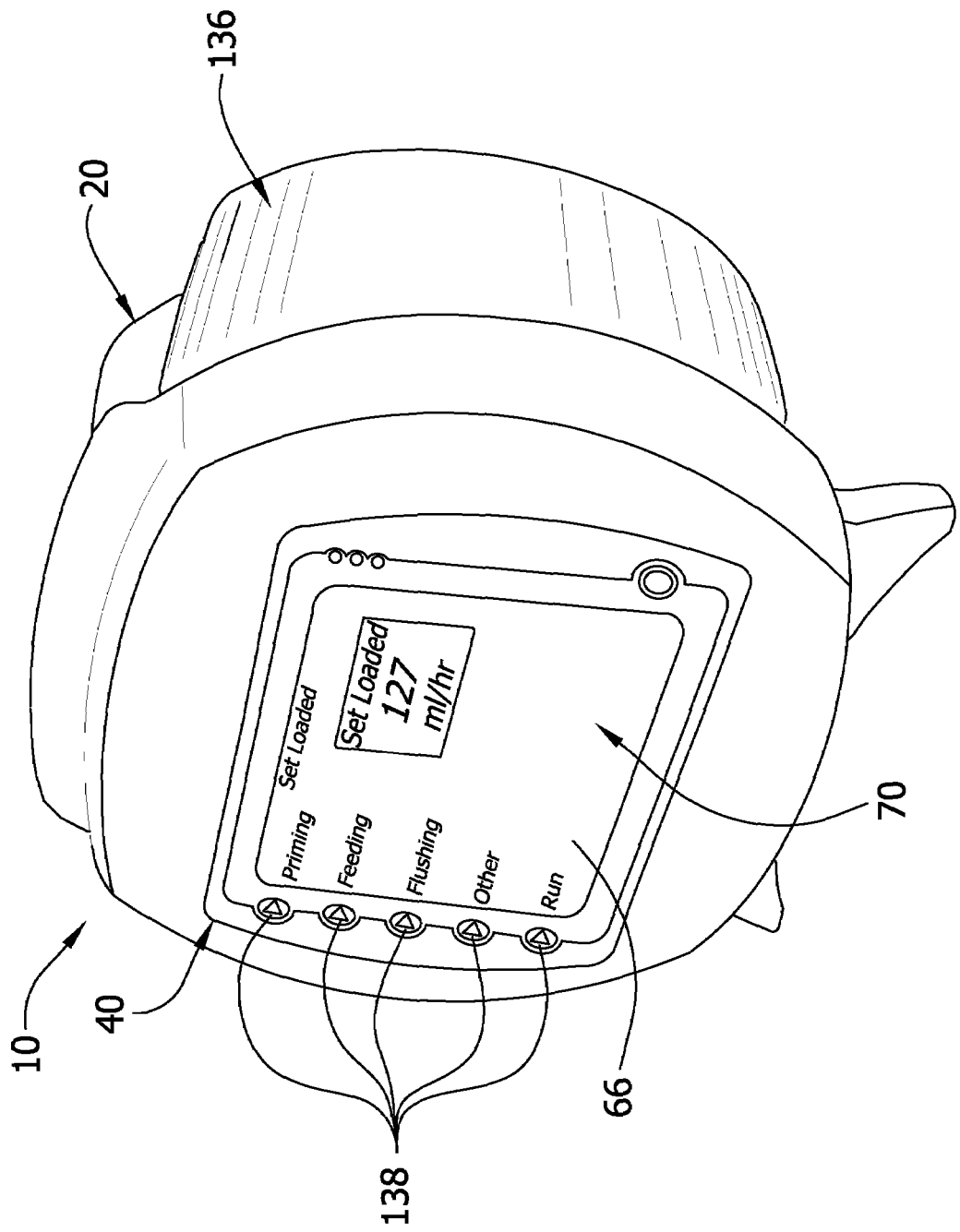
FIG. 1 is a perspective view of an exemplary flow control apparatus having a flow monitoring system according to the present invention.

Referring to the drawings, an embodiment of the flow control apparatus according to the present invention is illustrated and generally indicated as 10 in FIGS. 1-5. Flow control apparatus 10 comprises a flow monitoring system 12 that is capable of detecting and identifying between upstream and downstream flow conditions present within an administration feeding set 14. The administration feeding set 14 includes tubing 56 that is loaded to the flow control apparatus 10 for delivery of fluid to a patient by engaging a valve mechanism 26 and mounting member 74 of the administration feeding set 14 to the flow control apparatus 10. As used herein, the term load means that the valve mechanism 28 and mounting member 74 are engaged to the flow control apparatus 10 and tubing 56 is placed in a stretched condition between the valve mechanism 28 and mounting member 74 such that the administration feeding set 14 is ready for operation with flow control apparatus 10.

Figure 2:
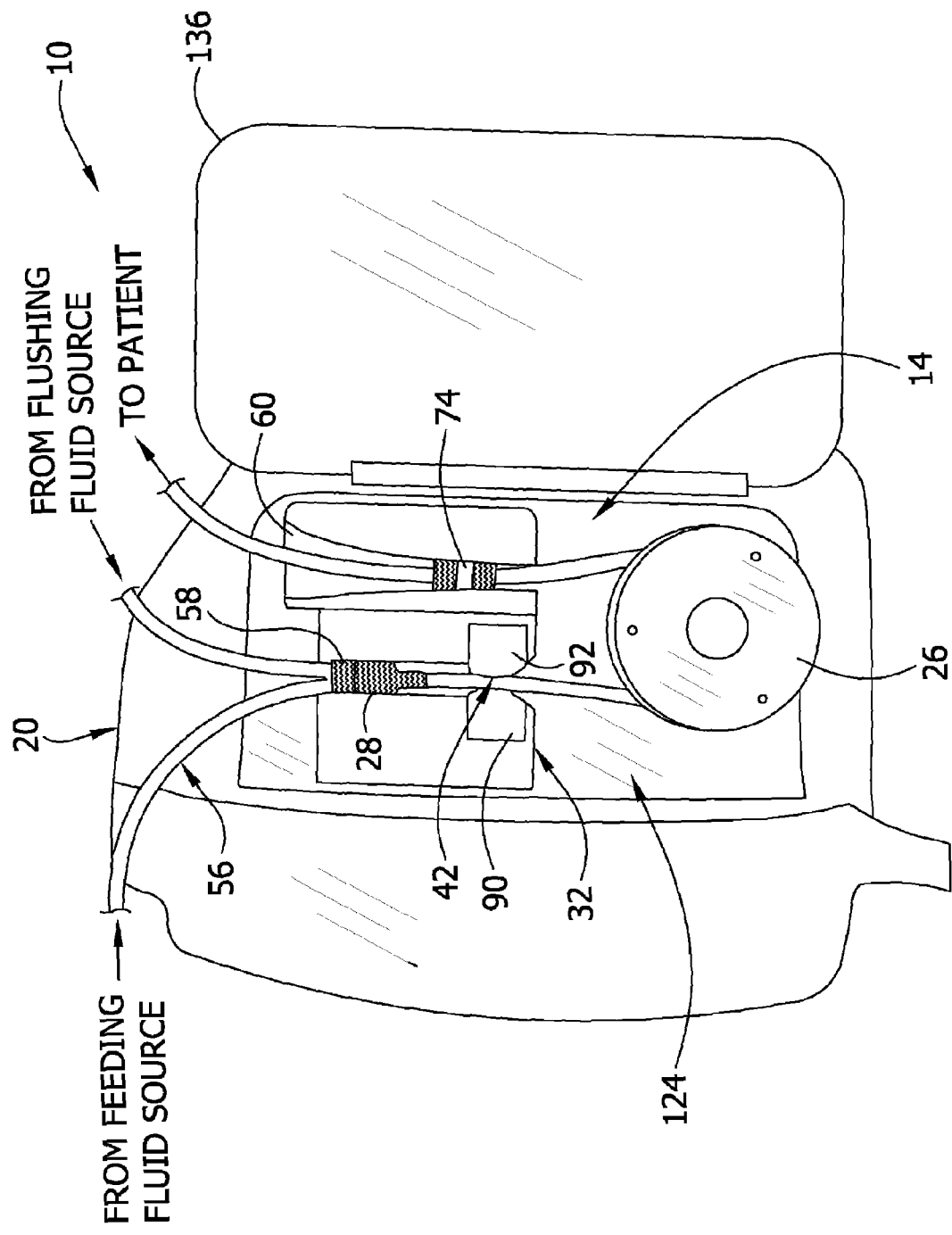
FIG. 2 is a side view of the flow control apparatus with an administration feeding set loaded thereto according to the present invention.

Referring to FIGS. 1 and 2, an exemplary flow control apparatus 10 according to the present invention comprises a housing 20 adapted for loading administration feeding set 14 to the flow control apparatus 10. Flow control apparatus 10 comprises a main recess 124 covered by a main door 136 and includes first and second recesses 58 and 60 for providing sites that are adapted to load the administration feeding set 14 to the flow control apparatus 10 when engaging the valve mechanism 28 and mounting member 74 to first and second recesses 58, 60, respectively. Preferably, a means for driving fluid, such as a rotor 26, is rotatably engaged through housing 20 and adapted to engage tubing 56 such that tubing 56 is placed in a stretched condition between first and second recesses 58, 60 when the administration feeding set 14 is loaded to the flow control apparatus 10.

As used herein, the portion of tubing 56 of administration feeding set 14 leading to rotor 26 is termed upstream, while the portion of tubing 56 leading away from rotor 26 is termed downstream. Accordingly, rotation of rotor 26 compresses tubing 56 and provides a means for driving fluid from the upstream to the downstream side of the administration feeding set 14 for delivery to a patient. The present invention contemplates that any flow control apparatus having a means for driving fluid may be used, such as a linear peristaltic pump, bellows pump, turbine pump, rotary peristaltic pump, and displacement pump. In addition, the present invention contemplates that a means for preventing fluid flow in the administration feeding set 14 is preferably valve mechanism 28; however any means that can prevent fluid flow through the administration feeding set 14 may be used.

Referring to FIG. 1, flow control apparatus 10 further comprises a user interface 40 that assists the user to operatively interface with the flow control apparatus 10. A display 70, in operative association with a plurality of buttons 138 positioned along an overlay 66, assist the user to interact with a microprocessor 62 to operate the flow monitoring system 12 according to the present invention.

Figure 3:
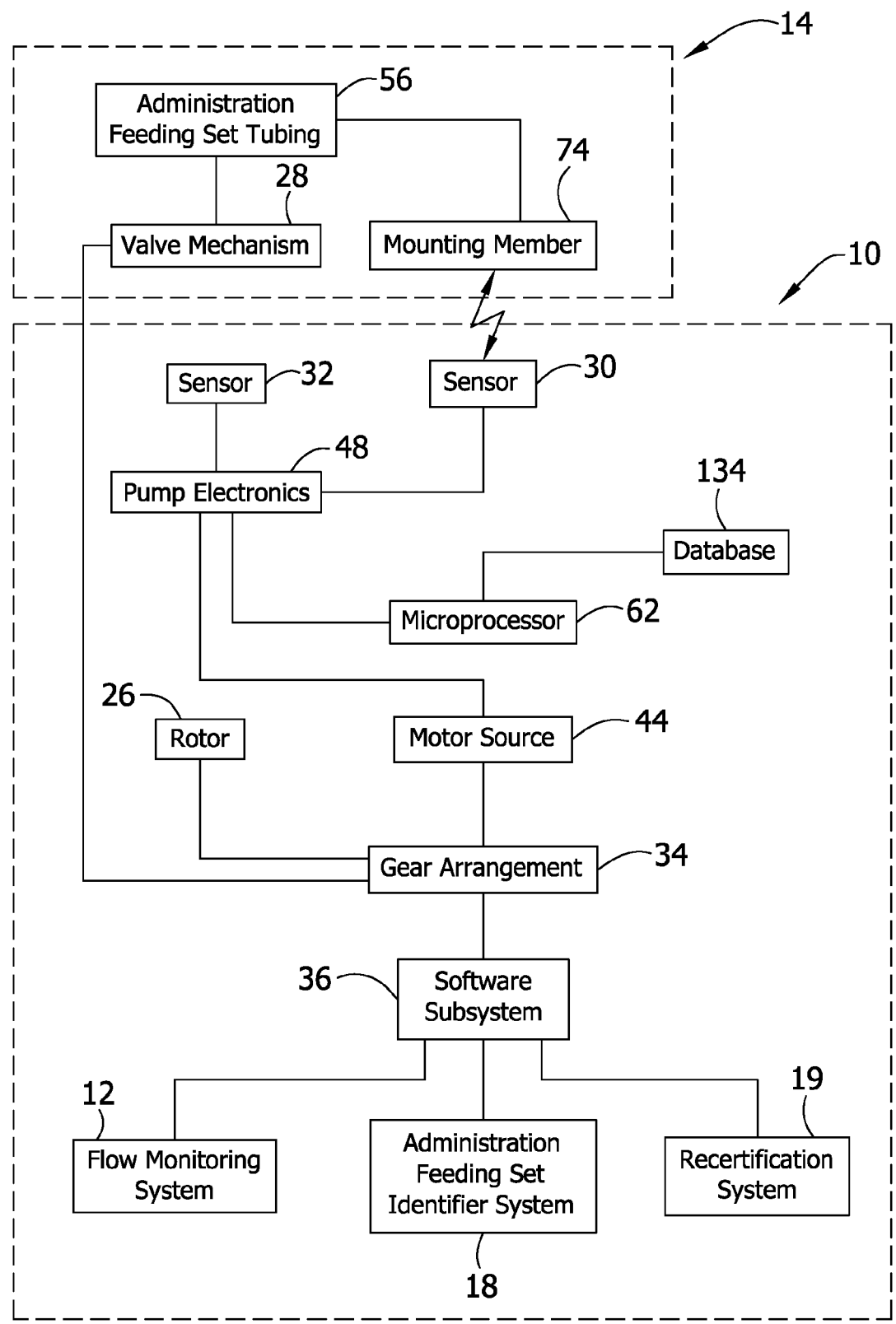
FIG. 3 is a simplified block diagram illustrating the elements of the flow control apparatus comprising a flow monitoring system according to the present invention.

Referring to FIG. 3, flow control apparatus 10 further comprises a microprocessor 62 in operative association with a single sensor 32. A software subsystem 36 is operatively associated with microprocessor 62 and is further associated with flow monitoring system 12 and a means for preventing fluid flow, such as valve mechanism 28, that provides a means for the flow control apparatus 10 to detect and identify between upstream and downstream flow conditions present in the administration feeding set 14 during operation of the flow control apparatus 10. As noted above, flow control apparatus 10 includes single sensor 32 for detecting whether fluid is present or absent in tubing 56 at the upstream side of the administration feeding set 14. The single sensor 32 is located on housing 20 of the flow control apparatus 10 and is positioned to detect the presence or absence of fluid in the upstream side of the administration feeding set 14. In an embodiment shown in FIG. 2, single sensor 32 is incorporated in a recessed sensor track 42 and is adapted to securely receive tubing 56 therein when the administration feeding set 14 is loaded to the flow control apparatus 10.

In order for single sensor 32 to detect the presence or absence of fluid in the tubing 56 of the administration feeding set 14 it is required that tubing 56 be engaged and retained within sensor track 42. In one embodiment, the engagement and retention of tubing 56 within sensor track 42 is achieved by activating flow control apparatus 10 when tubing 56 is empty of fluid and engaged around the flow control apparatus 10 such that a vacuum is created that decreases the outer diameter of tubing 56 as air is evacuated from the administration feeding set 14, thereby placing tubing 56 in a deflated state. In this deflated state, the user may easily insert tubing 56 within sensor track 42 when loading the administration feeding set 14 to the flow control apparatus 10.

Further, with tubing 56 empty of any fluid, a valve mechanism 28 connected to tubing 56 is engaged to the first recess 58, the tubing 56 then wrapped around rotor 26, and a mounting member 74 engaged to second recess 60 such that administration feeding set 14 is loaded to flow control apparatus 10 and the portion of tubing 56 between first and second recesses 58 and 60 is in a stretched condition. Valve mechanism 28 is then operated to allow fluid flow communication through tubing 56 such that air is evacuated from the administration feeding set 14. Thus, when the rotor 26 is made operational during this priming procedure a vacuum is created within tubing 56 forcing it to collapse due to the flexible nature of tubing 56 and lack of fluid contained in the administration feeding set 14. This temporary collapse of tubing 56 coupled with the tensile forces applied from operating rotor 26 allows tubing 56 to be easily retained within sensor track 42.

In addition, when the flow control apparatus 10 is operational and the tubing 56 engaged within sensor track 42, fluid flow through tubing 56 increases the outer diameter of tubing 56 relative to the inner diameter of the sensor track 42. Once the tubing 56 is engaged within sensor track 42 and the remaining portions of the administration feeding set 14 are engaged to flow control apparatus 10, the flow monitoring system 16 becomes operational.

Microprocessor 62 controls and manages the operation of the various components of the flow control apparatus 10. Preferably, single sensor 32 comprises an ultrasonic transmitter assembly 90 that transmits an ultrasonic signal through the portion of tubing 56 seated in the sensor track 42 to provide a means for detecting the presence or absence of fluid in the upstream side of the administration feeding set 14 when the signal is received by a receiver assembly 92. Upon receipt of the ultrasonic signal, receiver assembly 92 detects whether fluid is present or absent within tubing 56 along sensor track 42 based on the characteristics of the ultrasonic signal received by the microprocessor 62. The receiver assembly 92 then communicates with the microprocessor 62. Based on the characteristics of the received ultrasonic signal communicated to microprocessor 62 software subsystem 36 determines whether fluid flow within the administration feeding set 14 is normal or a flow abnormality exists.

Software subsystem 36 determines through a series of decision points and steps whether normal flow or abnormal flow conditions exist within tubing 56, and if an abnormal flow condition does exist, whether it is a bag empty condition, upstream occlusion, or a downstream occlusion.

Figure 4:
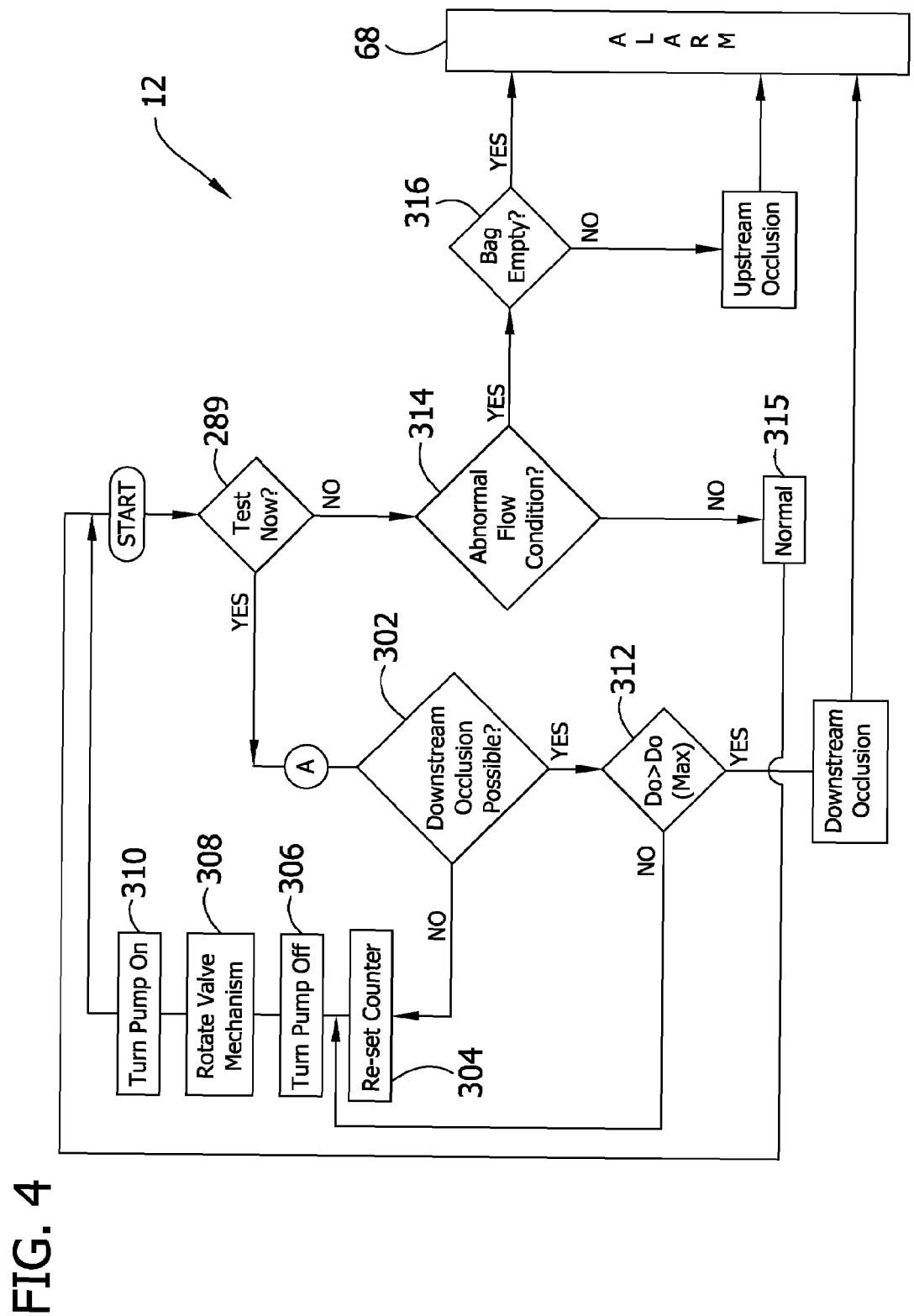
FIG. 4 is a flow chart of the flow monitoring system according to the present invention.
Figure 4A:
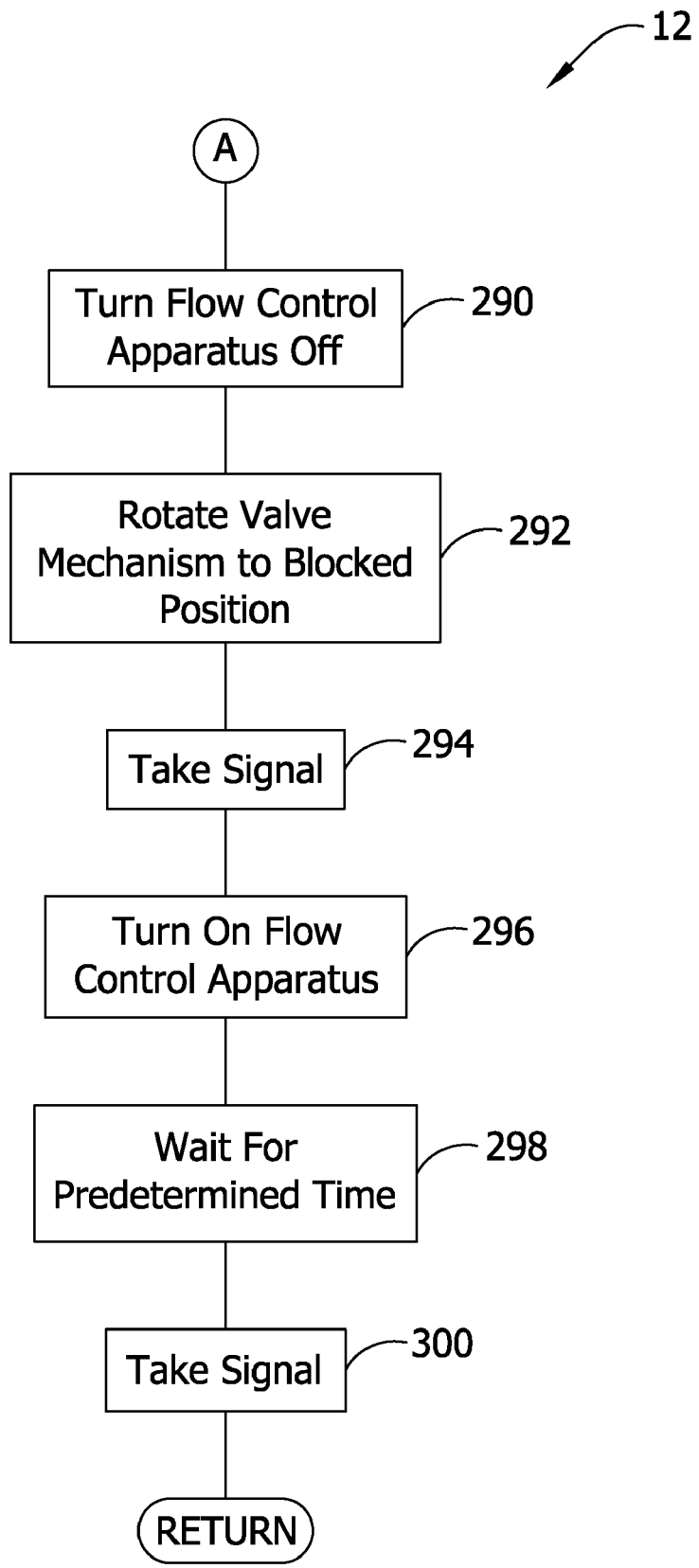
FIG. 4A is a sub-routine of the flow chart shown in FIG. 4 according to the present invention.

Referring to the flow charts in FIGS. 4 and 4A, the various decision points and steps executed by software subsystem 36 to perform an intermittent test procedure A by flow monitoring system 12 are illustrated. Software subsystem 36 directs flow control apparatus 10 to perform various operations related to detecting and distinguishing between upstream and downstream flow conditions present in the administration feeding set 14. During normal operation, single sensor 32 transmits ultrasonic signals through tubing 56 engaged within sensor track 42 for detecting the presence or absence of fluid in the administration feeding set 14. During operation of flow control apparatus 10 software subsystem 36 decides at predetermined times whether to initiate an intermittent test procedure A to determine whether a downstream occlusion exists. Intermittent test procedure A comprises terminating fluid flow communication through the administration feeding set 14 by valve mechanism 28, transmitting and detecting an ultrasonic wave for determining the presence or absence of fluid by single sensor 32 and a repetition of these steps, if necessary.

In particular, at step 289 software subsystem 36 decides whether to perform the intermittent test procedure A as illustrated in FIG. 4A. If so, the microprocessor 62 instructs flow control apparatus 10 to the OFF condition at step 290 in order to terminate operation of flow control apparatus 10 such that rotor 26 no longer drives fluid through tubing 56. At step 292, microprocessor 62 then places valve mechanism 28 in the blocking position that prevents fluid flow through tubing 56.

After fluid flow has been prevented through the administration feeding set 14 by valve mechanism 28, a baseline signal is taken by the single sensor 32 at step 294 for providing microprocessor 62 with a reading of the signal when the flow control apparatus 10 is reactivated at step 296. After re-activation, any fluid present within tubing 56 should be driven through tubing 56 by operation of rotor 26 and delivered to the patient as long as no occlusion is present along the downstream side of the administration feeding set 14. After a short period of time placement of valve mechanism 28 in the blocking position that terminates fluid flow should cause tubing 56 to run dry of any remaining fluid unless a downstream occlusion is present which would effectively prevent fluid from being delivered to the patient as fluid is forced to remain within tubing 56 due to the occlusion. Software subsystem 36, after a predetermined amount of time, permits any excess fluid to drain from tubing 56 at step 298. At step 300, single sensor 32 then transmits another ultrasonic signal through tubing 56 and takes a second reading to determine if fluid is present or absent within the administration feeding set 14. If fluid remains within the administration feeding set 14, software subsystem 36 then determines that a downstream occlusion is present and sounds an alarm.

Once intermittent test procedure A is completed, software subsystem 36 reaches a decision point 302 which determines whether or not a downstream flow condition, such as an occlusion along the downstream side of the administration feeding set 14 is present within tubing 56. If no fluid remains in tubing 56 at decision point 302, software subsystem 36 determines that no downstream occlusion is present. At step 304, microprocessor 62 re-sets the counter and places flow control apparatus 10 in an OFF condition at step 306. Valve mechanism 28 is then placed in either a feeding or flushing position that permits fluid flow through tubing 56 at step 308. After actuation of valve mechanism 28 to the feed or flush position flow control apparatus 10 is placed in the ON condition at step 310 and the flow monitoring system 12 has software subsystem 36 return to step 289.

If at decision point 302 an occlusion along the downstream side of the administration feeding set 14 is possible then decision point 312 is reached. Decision point 312 counts the number of occurrences that single sensor 32 detects the presence of fluid within tubing 56 which is referred to as $D_o$, while a pre-set maximum number of occurrences that flow monitoring system 12 allows for detection of a possible downstream occlusion being referred to as $D_o$ (max). If the $D_o$ is not greater than $D_o$ (max) at decision point 312 software subsystem 36 will determine that no downstream occlusion exists and valve mechanism 28 is placed in a position that permits fluid flow through the administration feeding set 14 in a manner as previously described above in steps 304, 306, 308, and 310. However, if $D_o$ is greater than $D_o$ (max) a downstream occlusion may exist and software subsystem 36 will direct microprocessor 62 to activate an alarm 68.

Preferably, alarm 68 may be audible, visual, vibratory or any combination thereof. In an embodiment of the present invention it is anticipated that a certain type of alarm 68 may represent a specific abnormal flow condition being present within administration feeding set 14 and identifiable to the user by its own unique visual, audible and/or vibratory alarm 68. For example, alarm 68 having different sounds could indicate different types of upstream and downstream flow conditions, such as a downstream occlusion, a bag empty condition, or an upstream occlusion. These unique alarms 68 allow for flow monitoring system 12 to signal the presence of several different abnormal flow conditions.

The detection of the upstream flow conditions present within administration feeding set 14, such as upstream occlusion or a bag empty condition, is determined by the presence or absence of fluid within tubing 56 by single sensor 32 at a detection point positioned on the upstream side of administration feeding set 14. However, unlike the detection of a downstream occlusion along the administration feeding set 14 the detection of an upstream flow condition, such as an upstream occlusion or bag empty condition, in the administration feeding set 14 does not require that the intermittent test procedure A be performed. Instead, the detection of these upstream flow conditions is accomplished during the normal operation of flow control apparatus 10 while valve mechanism 28 is in the feeding or flushing position that permits fluid flow through the administration feeding set 14.

Flow monitoring system 12 also detects and distinguishes between upstream flow conditions, such as normal flow, bag empty, and upstream flow occlusion conditions when the intermittent testing procedure A is not being performed by software subsystem 36. Specifically, at decision point 289 if software subsystem 36 does not initiate intermittent test procedure A for detecting downstream flow conditions software subsystem 36 will function to detect and distinguish between the conditions of normal flow, bag empty, and upstream occlusion.

Software subsystem 36 in operative association with flow monitoring system 12 determines whether or not a normal upstream flow condition exists within administration feeding set 14 during operation of flow control apparatus 10. This operation occurs at a decision point 314 and is determined based upon the presence or absence of fluid as detected by the single sensor 32. Specifically, if single sensor 32 detects the presence of fluid within tubing 56 then the flow is detected by software subsystem 36 at decision point 314. A normal upstream flow condition exists because a flow condition is not present that would occlude or obstruct fluid flow on the upstream side of the administration feeding set 14 that would cause fluid to become absent as detected by the single sensor 32. If flow is present at decision point 314 this normal flow condition would be displayed on user interface 40 at step 315. Accordingly, alarm 68 would not be activated since the patient would receive the correct dosage of fluid during flow conditions.

Figure 5A:
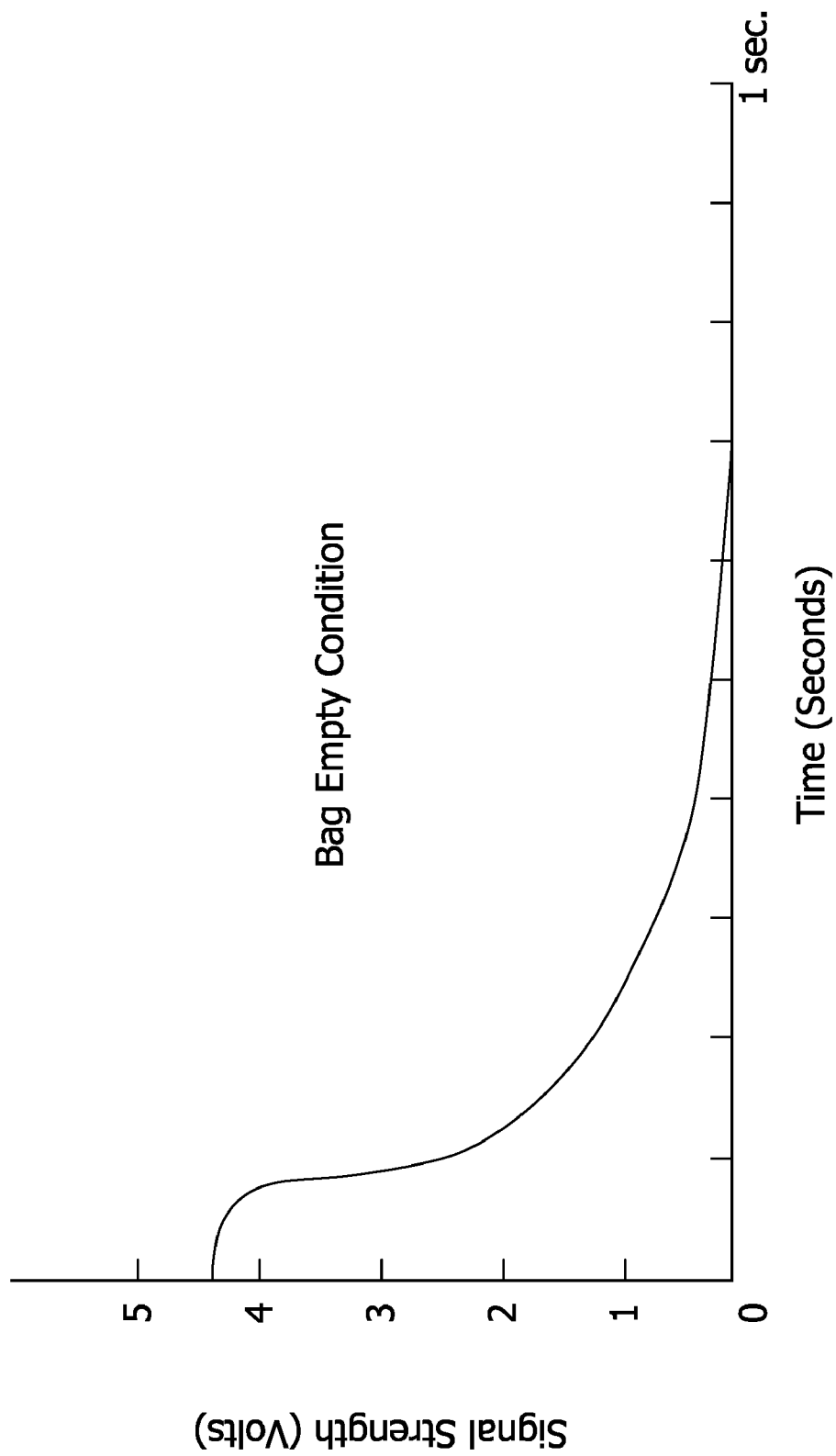
FIG. 5A is a graph illustrating the signal strength over time for a bag empty condition detected by the sensor according to the present invention.
Figure 5B:
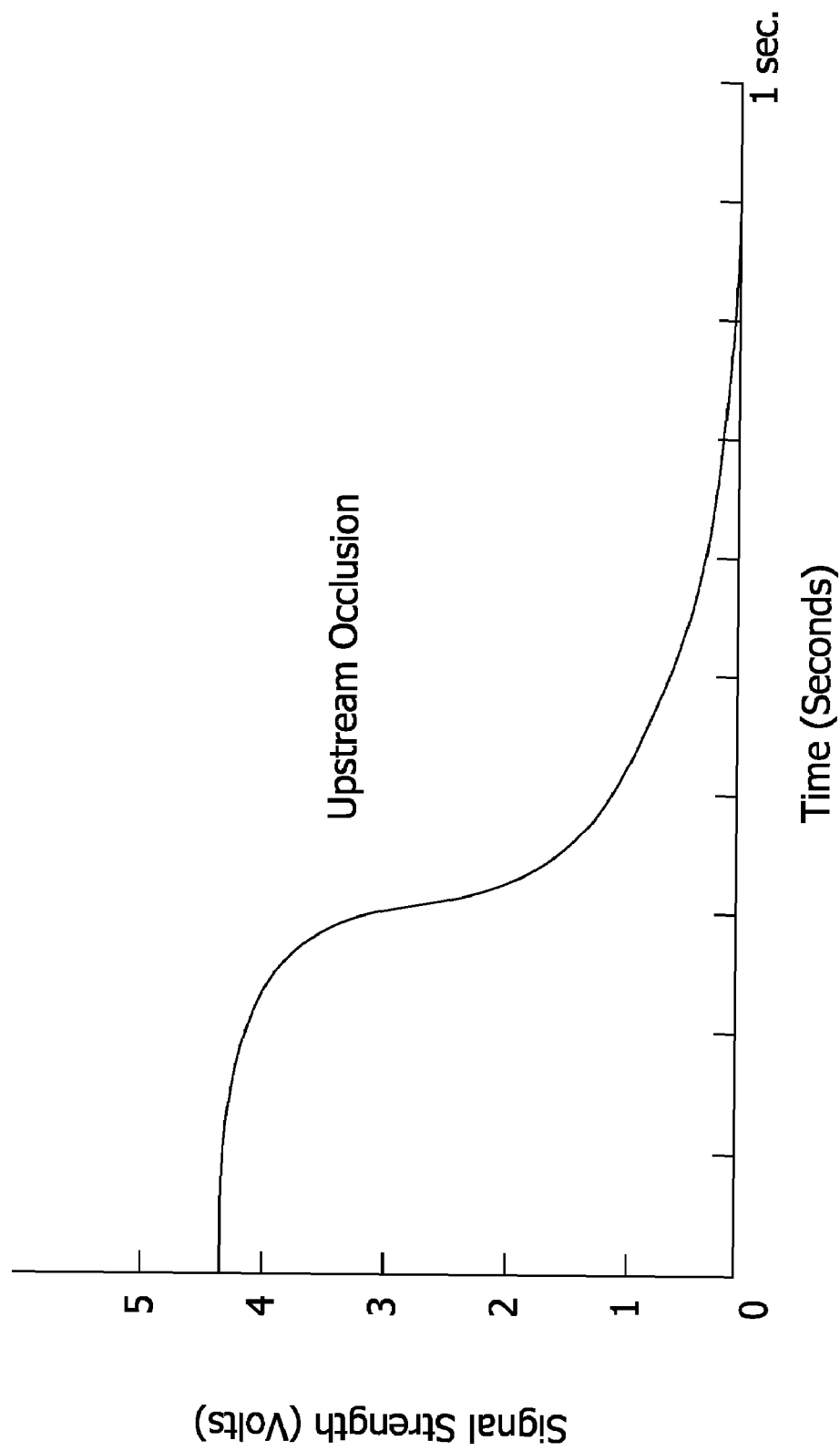
FIG. 5B is a graph illustrating the signal strength over time for an upstream occlusion detected by the sensor according to the present invention.

Flow monitoring system 12 only activates alarm 68 at decision point 314 if a bag empty condition or an occlusion along the upstream side of the administration feeding set 14 is detected as evidenced by the absence of fluid in tubing 56 during operation of the flow control apparatus 10. Software subsystem 36 distinguishes between bag empty condition and an upstream occlusion at decision point 316. As depicted in FIGS. 5A and 5B, a comparison is performed at decision point 316 in order to ascertain whether a bag empty condition or an upstream occlusion is present within administration feeding set 14.

As further shown, the graphs illustrated in FIGS. 5A and 5B provide predetermined baselines that represent the relative signal strengths of the ultrasonic signal received by the receiver assembly 30B for a bag empty condition and upstream occlusion, respectively, which provide a basis for distinguishing between these two upstream flow conditions based upon a comparison of a plurality of readings taken by single sensor 32 against the respective predetermined baseline criteria representative of these two flow abnormalities. In particular, software subsystem 36 compares the change of the signal strength from the plurality of sensor readings generated by single sensor 32 over time against the predetermined baseline criteria for these particular flow conditions. This provides a comparison with readings taken by single sensor 32 that permits the software subsystem 36 to distinguish between a bag empty and an upstream occlusion. For example, in a bag empty condition, the change between the subsequent readings would decrease more rapidly over time, while in an upstream occlusion the signal change would decrease more slowly over time. It should be noted that while the graphs in FIGS. 5A and 5B depict an example of a preferred baseline criteria, other baseline criteria which may distinguish these two flow abnormalities may be utilized.

Upon the determination that a bag empty condition is present at decision point 316 based upon signal comparison against the predetermined criteria as described above, software subsystem 36 activates alarm 68. If the software subsystem 36 determines at decision point 316 that an upstream occlusion is present, software subsystem 36 would also direct the activation of an alarm 68 indicative of such a flow abnormality.

Accordingly, the flow monitoring system 12 is capable of detecting and distinguishing between upstream and downstream flow conditions including at least four separate flow conditions that occur within an administration feeding set 14. The ability of the flow monitoring system 12 to detect and distinguish between upstream and downstream flow conditions is accomplished preferably by a single detection point by single sensor 32 positioned at the upstream side of the administration feeding set 14.

Figure 6A:
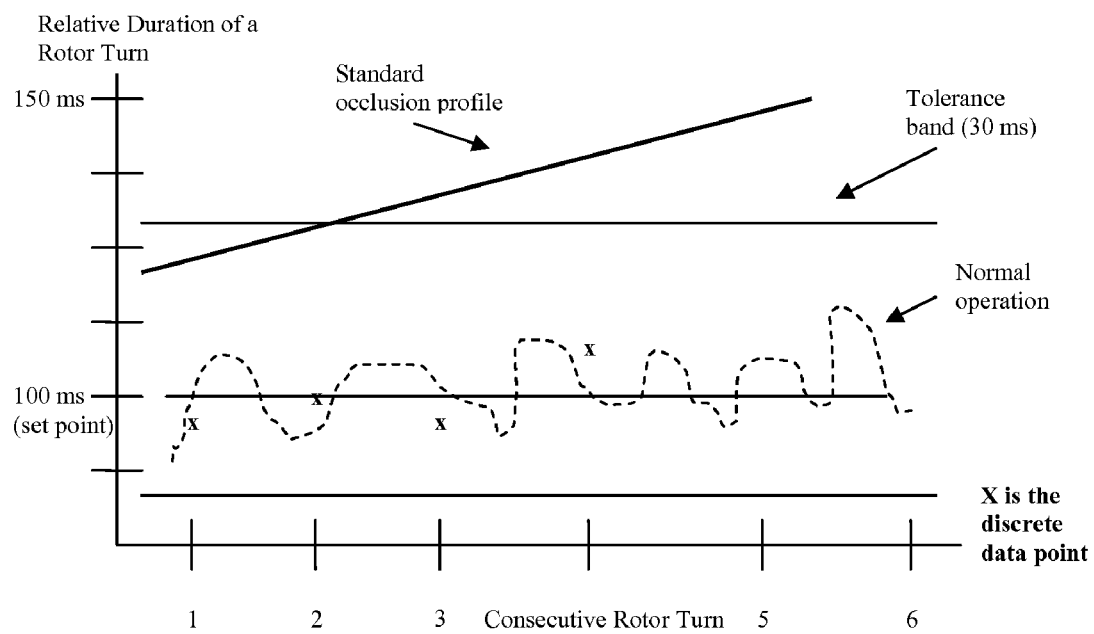
FIG. 6A is a plot of the relative rotor turn duration, operating within a tolerance band, versus the consecutive rotor turns, along with a standard occlusion profile.

FIG. 6A illustrates the flow control apparatus 10 operating within a proper tolerance. The discrete data points (described below) are the stars ("*"). The data points varying above and below a set point of 100 ms of the flow control apparatus 10. A tolerance band of +/−30 ms, for example, represents system noise, which can falsely trigger an occlusion indicator within the tolerance band. The tolerance band can be set other values depending on the motor or the required sensitivity. A sensitive application can be a syringe pump, requiring a tighter or lower tolerance. The standard occlusion profile is a straight line; however, a profile can be different to match the flow control apparatus 10 pumping characteristics.

To determine an occlusion or predict the occurrence of an occlusion, at least one discrete date point (described below), must be above the higher or lower limit of the tolerance band. The dashed line is the normal operation of the flow control apparatus 10 varying above and below the horizontal line at a 100 ms set point. The set point can change resulting in a change in the normal operation, tolerance band, and even the standard occlusion profile changes.

The concept of the present invention is monitoring, in software, the drag on the motor through a series of software calculations. Other prior art systems monitor directly the current or voltage use of the motor with software, to indicate an occlusion. These prior art systems suffer from not being flexible or accurate, in some high performance cases such as medical, to properly determine the presence or absence of an occlusion. The term consecutive rotor turns is meant to be one or more discrete data points in. succession, as determined by the program or user input (always possible with the LED screen at FIG. 1 at element 138). In other words, a rotor revolution turn can be skipped; however, the test will continue using the next available rotor revolution turn. The rotor revolution turn information could use rotor turn 1, 3, 5, and 6 to determine the presence of a downstream occlusion. The DSO Trigger test can cause the downstream occlusion test in FIG. 4 or sound an occlusion alarm 68.

Figure 6B:
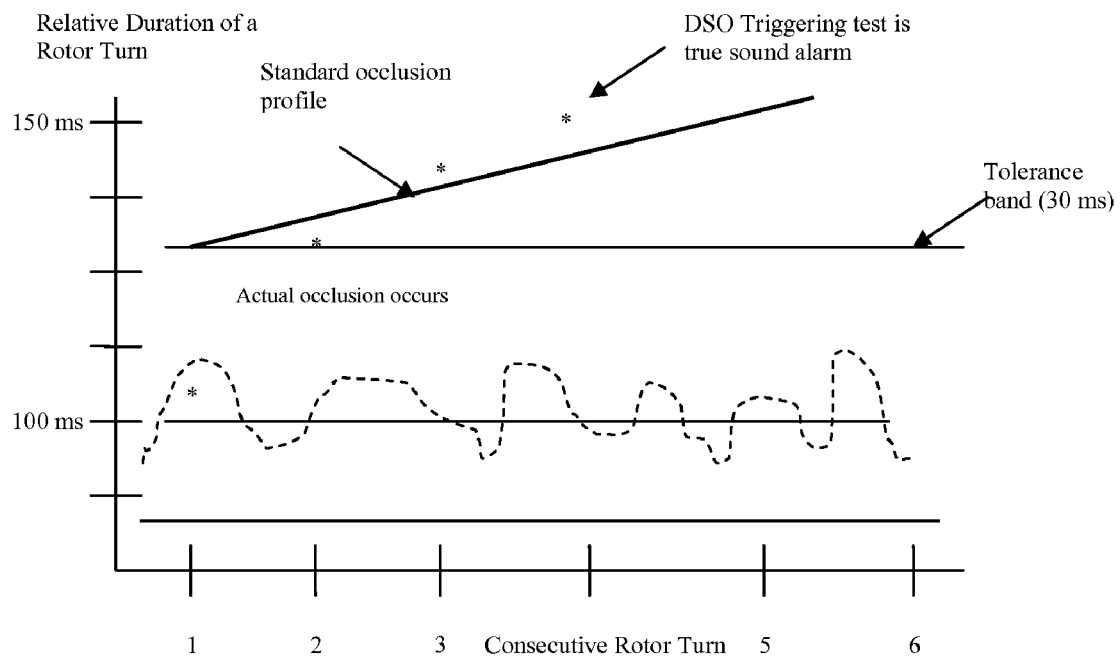
FIG. 6B is a plot representative of a standard occlusion profile similar to FIG. 6A, with a number of relative rotor turn durations computed during the flow apparatus operation.

FIG. 6B illustrates the standard occlusion profile plot. The plot is relative rotor turn duration, typically in mill-seconds (ms), plotted against the consecutive rotor turns measured in turns. The profile is independent of flow rate or the flow of a material or substance through the administration feeding set 14. Generally, a flow rate is based on the time between rotor turns and is dependent on the rotor 26 shaft speed and encoder counts.

An encoder (not shown) is attached to the rotor 26 shaft (not shown) and measured by the microprocessor 62. The number of signals from the encoder to the microprocessor 62, overtime indicates the speed. The number of encoder counts indicates a complete rotor turn. The DSO triggering test is measuring the relative revolution duration time of a rotor turn against a standard occlusion profile for the purpose of identifying an occlusion condition, not the flow rate. Once an occlusion detected condition is identified, the system sets the DSO Trigger variable (not shown), to TRUE and sets an occlusion alarm 68, or in the alternative embodiment exits to step 286 in FIG. 4 at step 1130A (described below), to perform the downstream occlusion test.

Figure 6C:
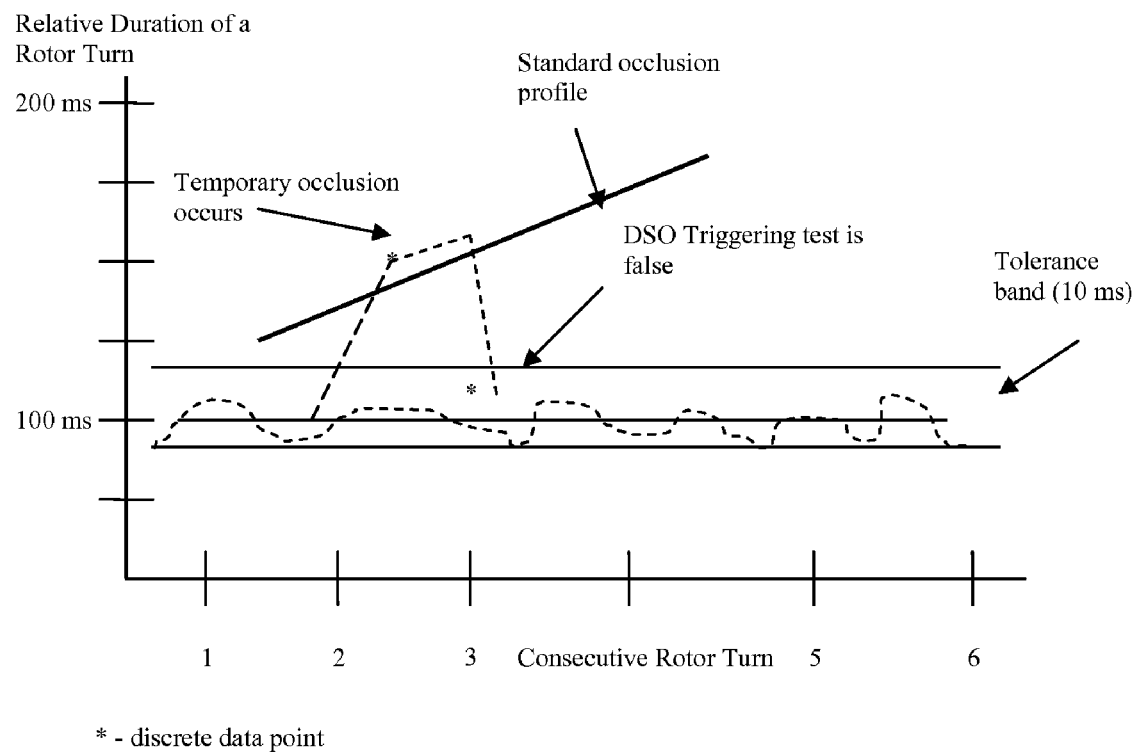
FIG. 6C is a temporary occlusion plotted against the standard occlusion profile similar to FIG. 6A.

FIG. 6C shows a temporary occlusion. The rotor revolution measured is plotted against the standard profile and compared against the rotor history of previous turns, filtered or otherwise, as shown in FIG. 6C. An increase in relative rotor revolution over one rotor turn may reduce at the next rotor turn at or near the tolerance band. This would represent a solid temporarily becoming lodged in the tubing, and if the number of NewTime readings is set at 1, the system may false alarm 68. Solids exist in formulae fed to a patient. The scale in FIG. 6C has been changed. This illustrates a design choice depending on the motor and other factors, such as sensitivity, accuracy and frequency of alarming required.

Figure 7:
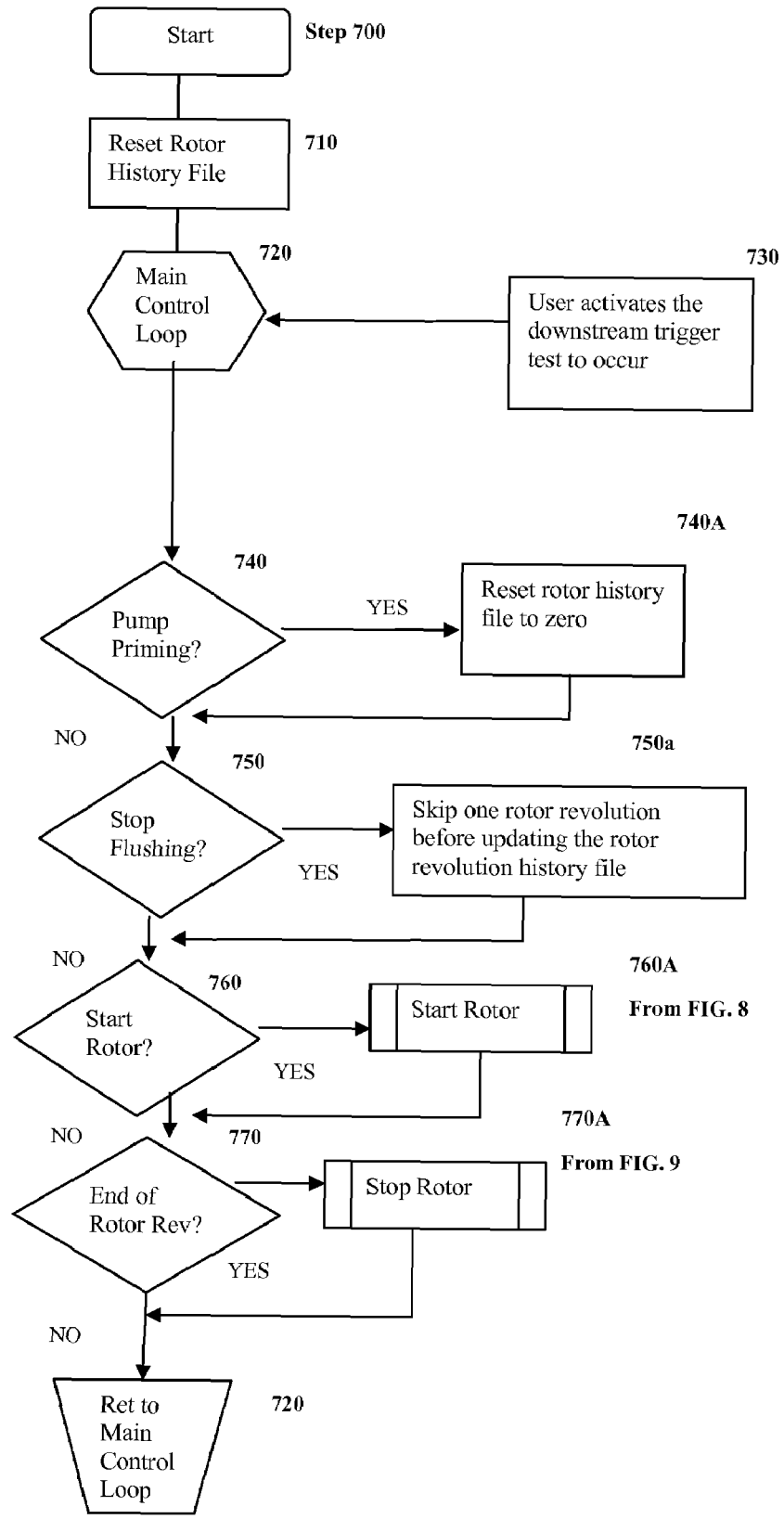
FIG. 7 is a flow chart of the main control loop of the downstream occlusion trigger test illustrated in FIG. 6B or FIG. 6C.

Referring to FIG. 7, the preferred embodiment of the invention for the flow control apparatus 10 is shown. This embodiment uses, among other things, an average of the rotor history file (determined at step 940C), to obtain the necessary repeatability and sensitivity required. An exemplary operation of the main control loop 720 is shown for the downstream occlusion trigger test or DSO Triggering test. A positive DSO Triggering without chaining (described below) triggers an occlusion alarm 68.

At step 700, the DOS trigger test is started. The test operates concurrently with the occlusion routine shown in FIG. 4. At step 710, the rotor history file is reset. The rotor history buffer or array is set to zero. The rotor history file or buffer has a number of, filterer or unfiltered, rotor revolution times, called NewTime below. At step 730, the user may manually invoke the DOSTriggering test. This is accomplished by depressing a key on the front of the flow control apparatus 10, or just entering the Running Mode screen in FIG. 1 at 138.

The DOCInterval time (not shown) sets the frequency at which the DSO Triggering test is run. For example, a DOCInterval set at 30 seconds means every 30 seconds the downstream occlusion test is executed. At step 740, the main control loop 720 determines if the flow control apparatus 10 is priming and resets the rotor history buffer to zero at step 740A. This means the main control loop can execute an occlusion check more quickly or less frequently, than the occlusion detection in FIG. 4 above.

At step 750, the main control loop 720 stops the flushing 750 activity, if flushing, and skips one rotor revolution because flushing occurs at high rate of speed. The one rotor revolution allows the system to stabilize. NewTime is the time of a rotor revolution, as discussed below. At 750A, the rotor revolution information is skipped, not the revolution itself.

Figure 8:
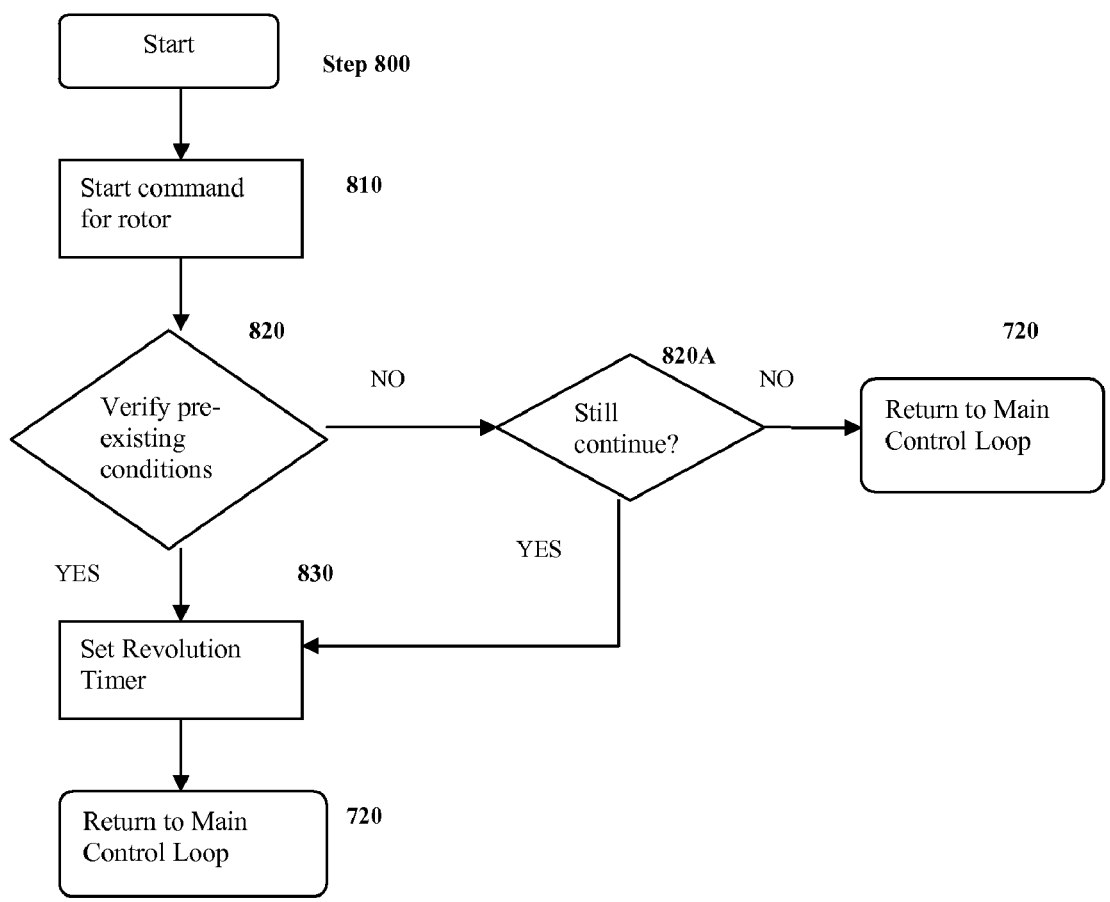
FIG. 8 is a flow chart of the start rotor routine at step 760 of FIG. 7.

At step 760, a stopped rotor is started at step 810 (FIG. 8). At step 830, a rotor revolution timer is started to measure the rotor revolution time, which is stored in NewTime. A rotor revolution time is measured using the system clock (not shown). The clock duration is measured after a fixed number of encoded signals are received at the microprocessor for a rotor revolution or a number of rotor revolutions, as specified in the DSO Triggering test. The clock duration is independent of the rotor turn.

An occlusion will drag the rotor, which will take the rotor 26 longer to make a revolution, as measured by the number of encoder signals returned to the microprocessor 62. The number of encoder signals is fixed at the time of manufacture for the flow control apparatus 10. So if a hundred encoder signals are needed per a rotor revolution, once the microprocessor receives the hundredth signal, the system clock time is measured and stored in memory. The difference of the start time, at step 830 and stop time at step 910 is stored in NewTime. This NewTime represents the rotor revolution duration for one rotor revolution. At step 820A, the system can still proceed to measure the rotor revolution time or NewTime, if the system overrides the failed conditions at step 820.

At step 820, a set of pre-existing conditions can be checked to determine if the current rotor turn is appropriate to measure for a rotor revolution time. This improves accuracy and helps avoid false occlusion alarms. The critical conditions may be the flow control apparatus 10 is not flushing, not priming, in a normal flow as opposed to super bolus mode, or no other system error exists. Once the conditions 820 are satisfied, the revolution timer 830 is started. The microprocessor 62 runs the timer 830, until the required number of encoder signals (as discussed in the preceding paragraph) are received.

Figure 9:
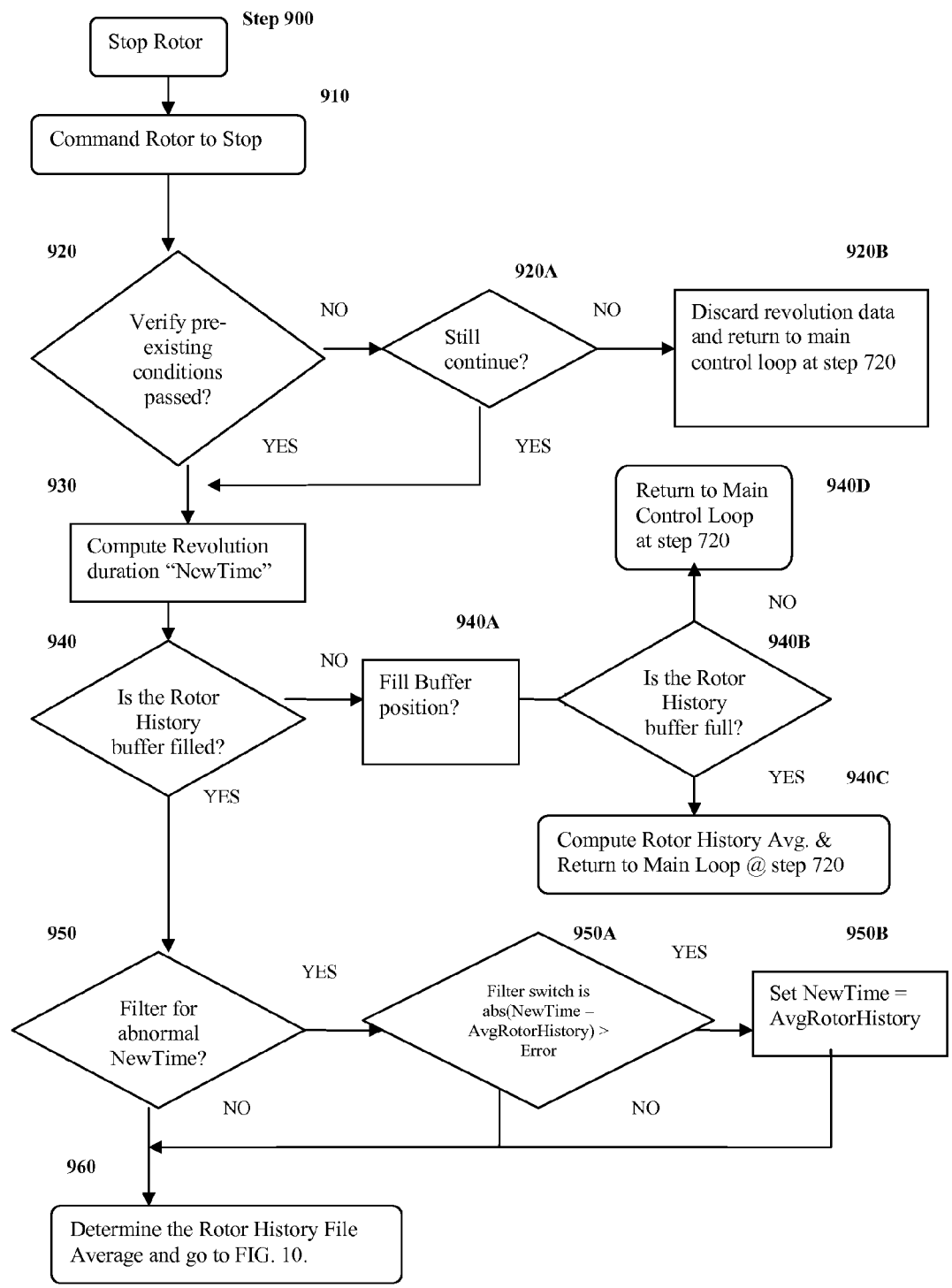
FIG. 9 is a flow chart of the stop rotor routine at step 770 of FIG. 7.

At step 770, the end of a rotor 26 revolution is determined, and if YES, the program exits to step 900 in FIG. 9. The command to stop the rotor is given at step 910. At step 920, a set of pre-existing conditions may be checked. The conditions are the same as in step 820. Additional conditions are rotor is off, or the current rotor revolution is not immediately following the downstream occlusion test because the measure is not reliable for averaging. If YES, the conditions are verified and control passes to step 930. If NO, at step 920A it is determined if the there is an override (Still Continue?), to use the rotor revolution for a NewTime, otherwise the rotor revolution information is discarded at step 920B and control returns to the main control loop at step 720.

At step 930, a NewTime is computed. The Revolution timer is stopped and stored in NewTime. Alternatively, the system clock time is stored in a buffer or temporary memory position. Then the clock time, at step 830, is subtracted from the clock time at step 930 and this difference is stored in NewTime, as discussed above in step 910.

At step 940, if the rotor history is filled, control passes to step 950. Otherwise, control is passed to step 940A and the buffer position is incremented. The rotor history position is updated with NewTime and control passes to step 940B. At 940B, if the rotor history array is filled, control passes to step 940C. At step 940C, a rotor history average is determined. The average is used to determine a discrete data point plotted on FIG. 6B, as shown. The discrete data point is NewTime less the rotor history average, provided the different is not greater than a Filter Error for NewTime (described below in step 950A). The discrete data point is the actual relative rotor revolution duration time, during flow control apparatus 10 operation. The data point is plotted on, FIG. 6B, to determine if an occlusion is happening.

Returning to step 940B, in this embodiment, the array is updated if there are still unfilled positions, which means the HistoryCount variable (not shown) is not zero. The HistoryCount variable is preset, when the history buffer is reset. The HistoryCount is not necessarily reset every time the downstream occlusion test is run.

The HistoryCount variable is counted down to determine the number of non-zero rotor revolution NewTimes' are stored in the history buffer, for averaging. The average of the rotor history buffer or file is used to determine if the system is trending in relative rotor revolutions. Trending higher indicates the system is occluded downstream, as illustrated in FIG. 6B. At step 940D, the rotor history buffer or array is not full, so exit to step 720.

An occlusion can occur for a variety of conditions. Material may settle from the feed solution at low feed rates. The sediment may collect and occlude the feeding set 14. The set 14 may become pinched as the patient rolls or moves.

After the rotor history buffer is full at step 950, the NewTime is filtered for an abnormal condition. An abnormal condition can occur if a person interferes with the rotor 26 or the rotor 26 jams. A person pinching the tubing 14 will cause an occlusion alarm 68

If the system is filtering (at step 950A), the filter switch is the absolute value of NewTime less the average of the rotor history buffer (AvgRotorHistory) greater than a Filter error. The Filter error is set in the program to be about 100 ms, and the Filter error depends on the flow control apparatus 10. The Filter error can be varied depending on the sensitivity of the flow control apparatus 10. At step 950B, an error or abnormal condition sets the NewTime to the current average of the rotor history file, previously determined at step 940A. No error or abnormal condition, the program determines the average history, at step 960, and passes controls to FIG. 10.

Figure 10:
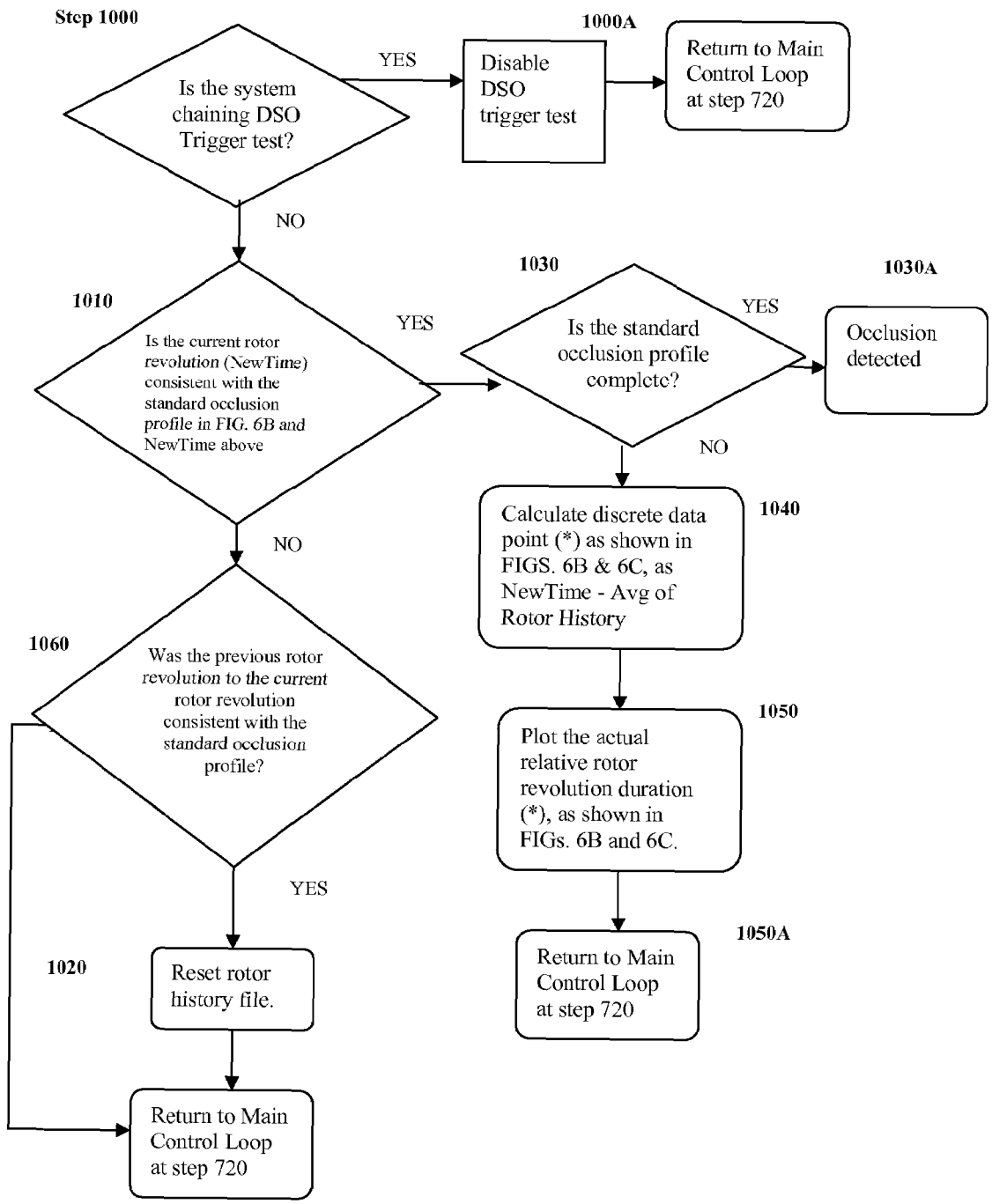
FIG. 10 is a flow chart of the occlusion found at step 960 of FIG. 9, for the first embodiment.

In FIG. 10, the system is identifying at least one NewTime that meets the standard profile in FIG. 6B. For improved accuracy, three NewTime values that meet the standard profile over three consecutive rotor turns will result in an occlusion detected condition. The first test step is to ensure the system is not chaining at step 1000.

At step 1000 in FIG. 10, the system is checked for chaining. Chaining is too many downstream occlusion checks within DOCInterval is occurring. For example, five downstream occlusion tests are caused within ten minutes, the system is chaining. At step 1000A, the downstream occlusion is disabled the system is reset and control passes to the main control loop at step 720.

At step 1010, the NewTime is determined to be consistent with the standard downstream occlusion profile and NewTime is above the upper tolerance, in FIG. 6B. At step 1060, step 1010 is not True or NO. At step 1010, the current rotor revolution is not matching the standard profile, so step 1010 exits to step 1060. At step 1060, the main control loop determines if the previous rotor revolution, to the current rotor revolution or NewTime, is consistent with the standard occlusion profile. If YES, then the main control loop detected two inconsistent rotor revolutions and will reset the rotor history file at step 1020. This is shown in FIG. 6C, with the temporary occlusion.

One skilled in the art will recognize, one inconsistent reading may introduce too many alarms, but a higher number may not alarm quickly enough. The number of inconsistent rotor revolutions, at step 1060 may be set with a counter, incremented or decremented, after step 1060. If the counter condition is meet, then the rotor history file is reset a step 1020.

At step 1040, NewTime, is converted to a discrete data point as NewTime less AvgRotorHistory. At step 1050, the discrete data point is compared to the standard occlusion profile, at FIG. 6B, over one or more consecutive rotor turns, as determined by the system Until the number of consecutive discrete data points are plotted, the system will exit to the main control loop at step 1050A.

At step 1030, the standard occlusion profile is complete, if at least one or more NewTime data points match the standard occlusion profile, for the one or more consecutive rotor turns. Referring to FIG. 6B, at rotor revolution turn one (1), the discrete data point at step 1040 matches the relative duration for the rotor turn at 110 ms or, outside of the tolerance band. The system does not consider this point possibly occluding. If a second discrete data point is used, this point is plotted at approximately 135 ms, at the second consecutive rotor turn. This point falls outside the tolerance band and indicates a possible occlusion is occurring. A third consecutive rotor turn may be required, at 140 ms, to set the DSO Triggering test to TRUE and to sound the occlusion alarm at step 1030A. The number of discrete data point matched to the standard occlusion profile, of FIG. 6, is dependent on the accuracy or number of false occlusion alarms, the user will tolerate for the flow control apparatus.

Figure 11:
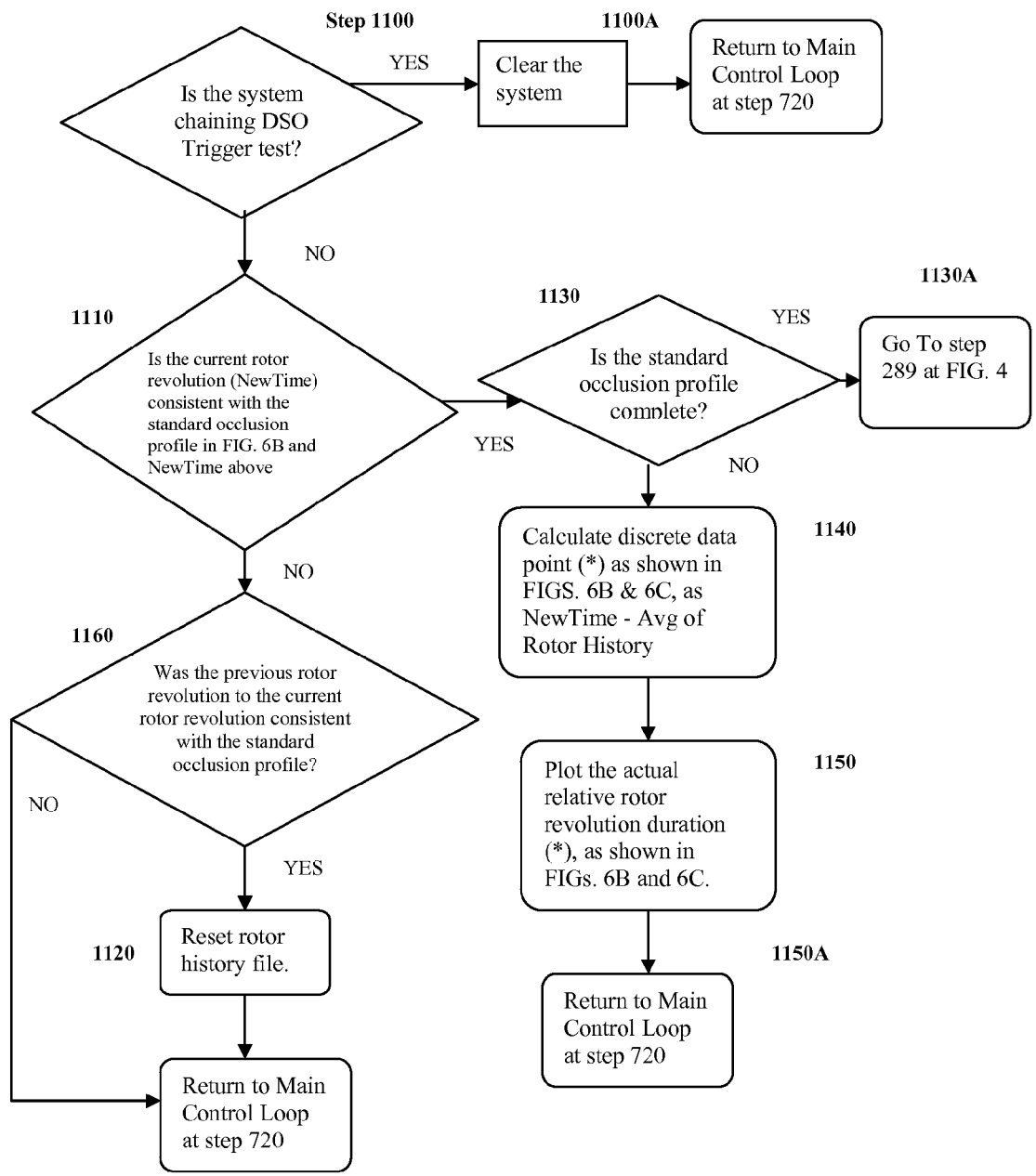
FIG. 11 is a flow chart of an occlusion found at step 960 of FIG. 9, for the alternative embodiment.

In an alternative embodiment in FIG. 11, the standard profile is determined complete at step 1130 and the main control loop exits to step 289 in FIG. 4, at step 1130A. This provides for another level of occlusion detection, which uses the standard profile, but actually determines the occlusion condition based on FIG. 4. Like steps have not been described between FIG. 10 and FIG. 11. For example, step 1020 is the same as step 1120. The reader is requested to refer to the description of the corresponding step in FIG. 10, for FIG. 11.

Although flow control apparatus 10 described above is an exemplary embodiment, the present invention contemplates that the flow monitoring system 12 may be used with any suitable flow control apparatus.

It should be understood from the foregoing that, while particular embodiments of the invention have been illustrated and described, various modifications can be made thereto without departing from the spirit and scope of the invention.

What is claimed is:

1. A flow control apparatus comprising:
    a) the flow control apparatus is adapted to be loaded with an administration feeding set having an upstream side and a downstream side, the flow control apparatus comprising a microprocessor;
    b) the microprocessor is configured to execute a software subsystem stored as computer-executed instructions, the software subsystem is capable of identifying a downstream occlusion present within the administration feeding set; and
    d) the software subsystem comprising a standard occlusion profile, the software subsystem plotting at least one discrete data point against a the standard occlusion profile wherein an occlusion detected condition is determined when the plotted data point matches the standard occlusion profile, and further wherein the step of plotting calculates a the discrete data point rotor revolution as NewTime less the average rotor revolution time.

2. The flow control apparatus according to claim 1, further comprising a sensor, the sensor in cooperation with the software subsystem determines the absence and presence of fluid in the feeding set.

3. The flow control apparatus according to claim 2, wherein said sensor comprises an ultrasonic transmitter assembly that transmits an ultrasonic signal through said administration feeding set, the sensor generates the discrete data point and wherein the signal is operative connected to the microprocessor.

4. The flow control apparatus according to claim 1, wherein the occlusion detected condition in cooperation with the software subsystem sounds an alarm.

5. A method of monitoring fluid flow comprising:
    a) loading an administration feeding set on a flow control apparatus;
    b) determining an average rotor revolution time;
    c) plotting at least one discrete data point against a standard occlusion profile;
    wherein the step of plotting calculates the discrete data point as rotor revolution NewTime less the average rotor revolution time; and
    d) identifying a downstream occlusion, wherein the step of identifying is the at least one discrete data point matching the standard occlusion profile for at least one rotor revolution.

* * * * *